United States Patent [19]

Braun et al.

[11] Patent Number: 5,723,561
[45] Date of Patent: Mar. 3, 1998

[54] PROCESS FOR THE CONTINUOUS PREPARATION OF ORGANOPOLYSILOXANES

[75] Inventors: Rudolf Braun, Kastl; Ludwig Hager, Burghausen; Johann Steiner, Kirchweidach; Horst Müller, Emmerting, all of Germany

[73] Assignee: Wacker-Chemie GmbH, Munich, Germany

[21] Appl. No.: 538,885

[22] Filed: Oct. 4, 1995

[30] Foreign Application Priority Data

Nov. 17, 1994 [DE] Germany ............ 44 41 057.3

[51] Int. Cl.⁶ .................................................. C08G 77/06
[52] U.S. Cl. .................................. 528/12; 556/462
[58] Field of Search .......................... 556/462; 528/12

[56] References Cited

U.S. PATENT DOCUMENTS

| | | | |
|---|---|---|---|
| 2,460,805 | 2/1949 | Britton et al. | 260/46.5 |
| 3,853,934 | 12/1974 | Siciliano et al. | 260/448.2 E |
| 4,128,568 | 12/1978 | Buchner et al. | 260/448.2 E |
| 4,599,437 | 7/1986 | Riederer | 556/462 |
| 4,792,596 | 12/1988 | Ottlinger et al. | 528/14 |
| 4,831,174 | 5/1989 | Elms | 556/451 |
| 5,245,067 | 9/1993 | Schneider et al. | 556/466 |
| 5,408,025 | 4/1995 | Thompson et al. | 528/12 |

FOREIGN PATENT DOCUMENTS

| | | |
|---|---|---|
| 0237597 | 9/1987 | European Pat. Off. |
| 0522443 | 1/1993 | European Pat. Off. |
| 3632875 | 4/1988 | Germany |

*Primary Examiner*—Margaret W. Glass
*Attorney, Agent, or Firm*—Martin Connaughton

[57] ABSTRACT

A process for the continuous preparation of organopolysiloxane by condensation and/or equilibration reaction of organosilicon compounds comprising in a first step
  conveying an organosilicon compound, catalyst which is solid in the reaction mixture at least at the reaction temperature and, optionally, additives continuously from the bottom upwards through a heated cylindrical reactor which is arranged in a standing position and whose contents can be agitated mechanically and in a second step
  passing the reaction mixture obtained after leaving the reactor at the upper end thereof continuously through a cylindrical reactor and in a third step
  freeing the reaction mixture obtained of catalyst after exit from the reactor.

8 Claims, 1 Drawing Sheet

PROCESS FOR THE CONTINUOUS PREPARATION OF ORGANOPOLYSILOXANES

FIELD OF INVENTION

The present invention relates to a process for the continuous preparation of organopolysiloxanes by condensation and/or equilibration reaction.

BACKGROUND OF INVENTION

Many continuous processes for preparing organopolysiloxanes are known. Solid catalysts are frequently used under the respective reaction conditions particularly in the preparation of low-viscosity siloxanes. For example, these can be used in the form of fixed-bed catalysts. References may be made to U.S. Pat. No. 4,792,596 (Wacker-Chemie GmbH; issued on Dec. 20, 1988) or the corresponding DE 36 32 875 A. An advantage of this procedure is that the catalyst does not have to be removed by special process steps such as filtration. A disadvantage is frequently the low space-time yield. Another possibility is offered by processes which use solid catalysts in a heterogeneous mixture with the other starting materials where the catalysts have to be removed from the product mixture after the reaction. Reference may be made to U.S. Pat. No. 4,599,437 (Wacker-Chemie GmbH; issued on Jul. 8, 1986) or the corresponding EP 237 597 A and U.S. Pat. No. 2,460,805 (Dow Chemical Co.; issued on Feb. 8, 1949).

SUMMARY OF INVENTION

The present invention provides a process for the continuous preparation of organopolysiloxanes by condensation and/or equilibration reaction of organosilicon compounds, which comprises in a first step
conveying an organosilicon compound, catalyst which is solid in the reaction mixture at the reaction temperature and, optionally, additives continuously from the bottom upwards through a heated cylindrical reactor RI which is arranged in a standing position and whose contents can be agitated mechanically and in a second step
passing the reaction mixture obtained after leaving the reactor RI at its upper end continuously through a cylindrical reactor RII and in a third step
freeing the reaction mixture obtained of catalyst after exit from the reactor RII.

In the present invention, the term organopolysiloxanes also includes oligomeric and dimeric siloxanes.

Condensation reactions of organosilicon compounds are, in particular, the reactions of two Si-bonded hydroxyl groups with elimination of water, for example, the reaction of an Si-bonded hydroxyl group with an Si-bonded alkoxy group with elimination of alcohol or with Si-bonded halogen with elimination of hydrogen halide.

For the purposes of the present invention, equilibration reactions are the rearrangements of siloxane bonds of siloxane units.

Condensation and equilibration reactions frequently proceed simultaneously.

The organosilicon compounds used according to the invention are preferably linear or essentially linear diorganopolysiloxanes having Si-bonded hydroxyl groups and/or diorganopolysiloxanes end-blocked by triorganosiloxy groups, optionally in admixture with cyclic diorganopolysiloxanes.

Organosilicon compounds which can be used in the process of the invention are generally known and are frequently represented by the formulae

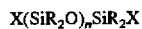 (I),

 (II)

and

 (III), where
R is identical or different and is a monovalent, unsubstituted or substituted hydrocarbon radical,
X is a hydroxyl group, an alkoxy group, chlorine or the group —OSiR$_3$, where R is as defined above,
n is 0 or an integer of at least 1, preferably 0 or an mean number from 1 to 150, and
m is an integer having a value from 3 to 60, preferably from 3 to 20.

Although not shown by the formulae frequently used, up to 10 mole % of the diorganosiloxane units can be replaced by other siloxane units such as RSiO$_{3/2}$ and/or SiO$_{4/2}$ units, where R is as defined above.

The radical R is preferably a hydrocarbon radical having from 1 to 18 carbon atoms, with hydrocarbon radicals having from 1 to 4 carbon atoms being more preferred, in particular the methyl radical.

Examples of monovalent hydrocarbon radicals R are alkyl radicals such as the methyl, ethyl, n-propyl, iso-propyl, n-butyl and sec-butyl radical, alkenyl radicals such as the vinyl and the allyl radical, and aryl radicals such as the phenyl and the naphthyl radical.

Examples of monovalent, substituted hydrocarbon radicals R are cyanoalkyl radicals, such as the group β-cyanoethyl radical, haloalkyl radicals such as the 3,3,3-trifluoropropyl radical, and haloaryl radicals such as o-, m- and p-chlorophenyl radicals.

In the process of the invention, particular preference is given to using those organopolysiloxanes of formula (I) where X=a hydroxyl group.

The viscosity of the organopolysiloxanes of formula (I) used in the process is preferably between 10 and 250 mm$^2$/s at a temperature of 25° C., more preferably between 20 and 150 mm$^2$/s.

Examples of compounds of formula (I) are α,ω-dihydroxydimethylpolysiloxane having a viscosity of 60 mm$^2$/s at 25° C., α,ω-dihydroxydimethylpolysiloxane having a viscosity of 110 mm$^2$/s at 25° C. and α,ω-bis(trimethylsiloxy)polydimethylsiloxane having a viscosity of 35 mm$^2$/s at 25° C.

Examples of compounds of formula (II) are hexamethylcyclotrisiloxane, octamethylcyclotetrasiloxane and decamethylcyclopentasiloxane.

Examples of compounds of formula (III) are hexamethyldisiloxane and 1,3-divinyl-1,1,3,3-tetramethyldisiloxane.

The compounds of formula (I) where X=—OSiR$_3$, where R is defined above, and disiloxanes of formula (III) are organosilicon compounds which regulate the chain length.

The amount of chain length-regulating organosilicon compound which is used depends on the desired molecular weight of the organopolysiloxanes prepared by condensation and/or equilibration, and is already known.

The organosilicon compounds used in the process of the invention can each be one type of such organosilicon compounds or a mixture of different organosilicon compounds.

In the process of the invention, the organosilicon compound used is preferably a mixture of organopolysiloxanes of formula (I) where X=a hydroxyl group and cyclosiloxanes of formula (II) or a mixture of organopolysiloxanes of formula (I) where X=—OSiR$_3$ having R as defined above and disiloxane of formula (III).

The above meanings of R and X respectively apply in their full scope to the SiC-bonded organic radicals and to the Si-bonded radicals of the other organosilicon compounds.

The organosilicon compounds used according to the invention are commercial products or can be prepared by methods customary in silicone chemistry.

The catalysts used in the process of the invention, are solid in the reaction mixture at least at the reaction temperature, can be the same ones as in the previously known processes for preparing high molecular weight organosilicon compounds.

Examples of catalysts which promote the condensation or the equilibration reaction are acid-activated bleaching earths such as acid-activated calcium bentonite, obtainable under the trade name "Tonsil" from Südchemie AG, sulfonated coal, acid-activated carbon black, cation-exchange polymers having side chains containing sulfonyl groups as ion-exchange sites, with the sulfonyl groups each being bonded to a carbon atom bearing at least one fluorine atom, and other cation-exchange polymers, in particular cation-exchange macrocrosslinked polymers, for example a pulverulent or granular macrocrosslinked polymer having sulfonyl groups as ion-exchange sites.

The catalysts used in the process of the invention are preferably acid-activated bleaching earths, in particular acid-activated calcium bentonite.

It is possible to use one type of catalyst or a mixture of various types of catalysts.

The mean particle size of the catalysts used in the process of the invention is preferably at most 1000 μm, more preferably from 2 to 200 μm.

The mount of catalyst used can be the same as in previously known processes for preparing organopolysiloxanes.

Preferably, catalysts for promoting condensation and/or equilibration reactions of organosilicon compounds are used in amounts of up to 10% by weight, more preferably from 1% to 4% by weight, based on the weight of the organosilicon compound to be condensed and/or to be polymerized.

In the process of the invention, it is further possible to use customary additives such as solvents, filter aids and other auxiliaries.

In the process of the invention, the organosilicon compound, catalyst and any additives used can be introduced separately into the reactor RI. However, preference is given to introducing a pumpable mixture of the organosilicon compound, catalyst and any additives used at the lower end of the reactor RI used. This pumpable mixture is preferably prepared by mixing the starting materials used according to the invention with one another in a vessel, optionally with heating.

Prior to introducing the organosilicon compound or the starting material mixture not already preheated during mixing into the reactor RI, the latter is preferably heated up to a temperature of 160° C., in a heat exchanger.

Both reactor RI and reactor RII each have a ratio of length to internal diameter of preferably from 1:1 to 50:1, more preferably from 1:1 to 20:1, in particular from 2:1 to 15:1. Both reactors preferably have a cylindrical tubular geometry, with deviations from this geometry being possible. The reactors are preferably heated by a jacket around each pipe. However, heating can be omitted for reactor RII if reactor RII is sufficiently well insulated.

The reactors used in the process of this invention are preferably heated to such a degree that the temperature of their content is from 50° to 200° C., in particular from 70° to 160° C., with the contents of reactor RI preferably having the same or about the same temperature as the contents of reactor RII.

The reaction mixture of reactor RI is preferably stirred. This can be carried out by means of a suitable stirrer with which the reactor RI can be equipped. An example of a suitable stirrer is a blade stirrer.

If, in the process of the invention, the reaction mixture is stirred, this is preferably carried out at a stirring speed of from 60 to 1000 revolutions per minute.

In the process of the invention, the reaction mixture flows through reactor RI from the bottom upwards and leaves reactor RI at its upper end, with the mean residence time in reactor RI preferably being from 2 to 20 minutes. There is located above the outlet for the mixture of organopolysiloxane, catalyst and any additives used exiling from the reactor RI a condenser and, optionally, a water separator in which the water formed in the condensation of Si-bonded hydroxyl groups and volatile organosilicon compounds are condensed and separated. Preferably, the water is discharged from the system and the organosilicon compounds distilled off are fed back into the process either directly or at a later point in time.

The reaction mixture exiting at the upper end of reactor RI is then, optionally by means of a pump, conveyed to reactor RII.

If reactor RI and reactor RII are operated at the same pressure, the outlet of RI can be directly connected to the inlet of RII. If the two reactors are to be operated at different pressures, it is advantageous to convey the reaction mixture from RI to RII by means of a pump.

Reactor II is preferably arranged in a standing position. However, it can also be arranged in a lying position.

In the process of the invention, the reaction mixture preferably flows through reactor RII from the top downwards and leaves reactor RII at its lower end, with an outlet for volatile compounds such as water and volatile organosilicon compounds being located at the upper end of the reactor RII, which can, in a similar manner to reactor RI, be connected to a condenser and water separator. If reactor RI and reactor RII are operated at the same pressure, the outlet located at the upper end of reactor RII is preferably connected with the condenser and any water separator of RI.

According to process variant A, the reactor RII is filled with reaction mixture, which corresponds to a long residence time in the reactor RII. This can be achieved by, more parts by volume being fed in at the upper end of RII than are taken off at the lower end, at the commencement of the continuous process. In this process variant, the reaction mixture of reactor RII can be stirred. For this purpose, reactor RII can be equipped with the same stirrer as reactor RI.

According to process variant B, the reactor RII is empty, i.e., not filled with reaction mixture. In this context, "empty" describes a state which is achieved by, reactor RII containing no reaction mixture and at the commencement of the continuous process, as many parts by volume are fed in per unit time at the upper end of RII as are taken off at the lower end.

In process variant B, it is advantageous if reactor RII contains internal fittings or packings which are inert to the reaction mixture, for example distributor trays, column packing and deflector elements, which lead to an increase in the surface area of the product stream flowing through the reactor.

In the process of the invention, preference is given to variant B.

It is self evident that, in the process of the invention, any variant lying between variants A and B is possible. This can be achieved, in particular, by variation of the ratio of reaction mixture fed in at the top to that taken off at the bottom in reactor RII. Thus, for example, process variant A is changed into process variant B by more product mixture being taken off at the lower end of RII than is fed in at the upper end. Process variant B can be changed into process variant A by less product mixture being taken off at the lower end of RII than is fed in at the upper end.

The pressures used in the process of the invention can be the same as previously known processes for preparing organopolysiloxanes. Depending on the type of starting materials used and on the reaction temperature selected as well as on the properties of the product, the pressures used can range from 0.1 to 1100 hPa. When nonvolatile starting materials are used, for example, linear organopolysiloxanes having terminal hydroxyl groups and/or triorganosilyl groups, it is advantageous to carry out the process of the reaction at low pressures such as from 0.1 to 100 hPa, by which means volatile constituents such as water can be effectively removed. On the other hand, when large amounts of volatile starting materials are used, such as cyclic siloxanes or disiloxanes, it is advantageous to carry out the process of the invention at the pressure of the surrounding atmosphere, i.e., from about 900 to 1100 hPa.

Reactor RI is preferably operated at the same pressure as reactor RII.

The mixture discharged from the reactor RII can be freed of catalyst in any manner which is suitable and well known for removing solids from suspensions, for example filtration or centrifugation, which is preferably carried out continuously. The catalyst is preferably removed by filtration. Optionally, filter aids such as kieselguhrs, celluloses and aluminosilicates can be used for this purpose. These can be added directly prior to the filtration. However, they can already be present in the reaction mixture. The catalyst separated off in this way can, if desired after mixing with fresh catalyst, be reused in the process of the invention.

The organosilicon compounds having boiling points lower than that of the desired organopolysiloxane and any additives used, can be removed by distillation from the organopolysiloxane freed of the catalyst. The compounds distilled off, in particular the low-boiling organosilicon compounds, can be reused as starting material.

The process of the invention gives organopolysiloxanes having a viscosity in the range from preferably 5 to 50,000 mm$^2$/s.

Optionally, the organopolysiloxanes prepared can be subjected to a purification process as described in EP 522 443 A (Wacker-Chemie GmbH, published on Jan. 13, 1993), with these being treated after their preparation with elemental copper, by means of which impurities resulting from the preparation can be removed.

DETAILED DESCRIPTION OF THE DRAWINGS

Figure 1:
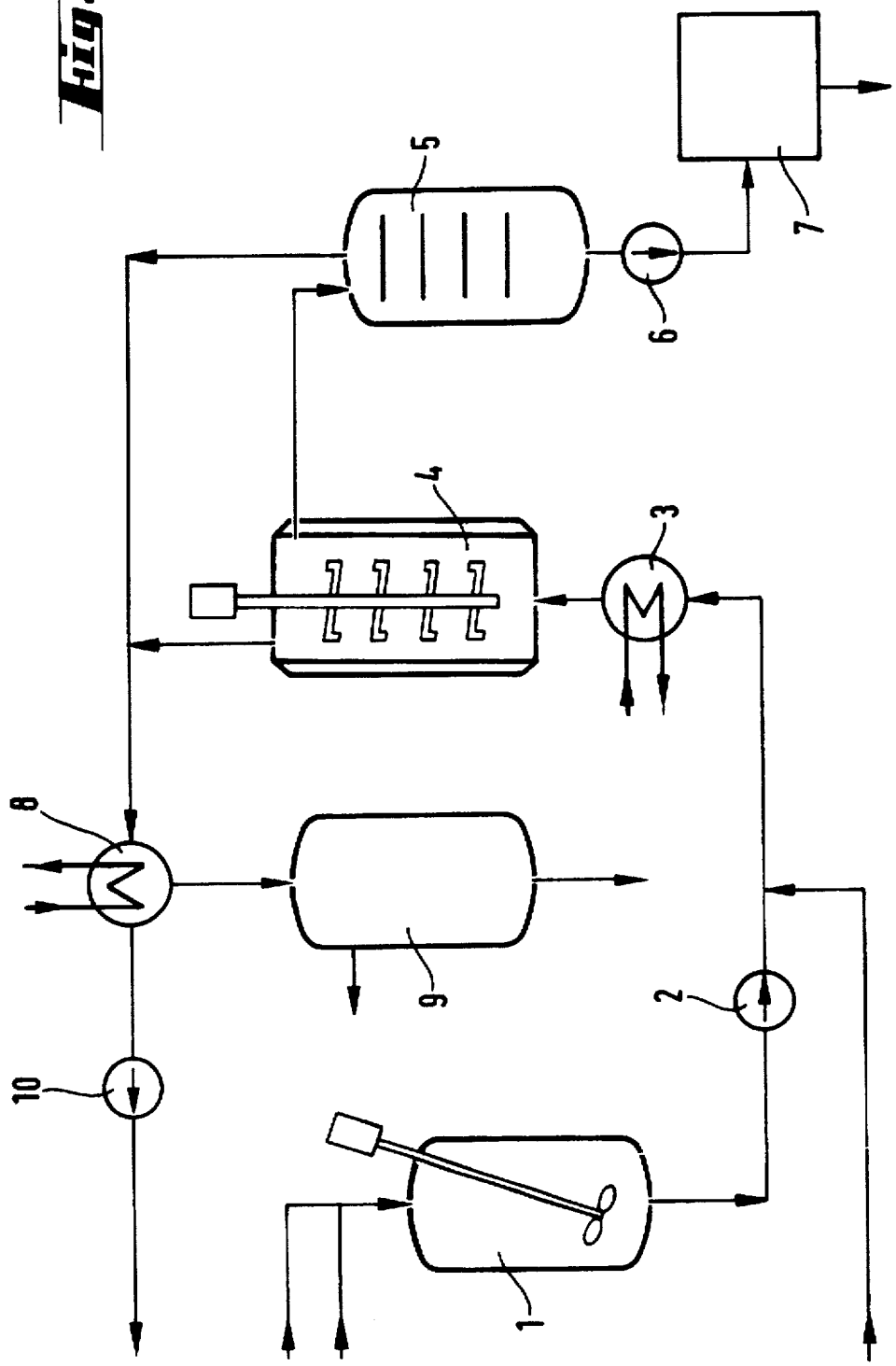
FIG. 1 illustrates the reaction steps in the instant process.

A preferred embodiment of the process of the invention is illustrated in FIG. 1, where in a first step mixing organosilicon compound, catalyst, more preferably acid-activated bleaching earth, and, optionally, additives with one another in a make-up vessel (1) while stirring, then heating the reaction mixture thus obtained via a preheater (3) using a pump (2), with any siloxane of formula (III) used being metered into the line after the make-up vessel, and conveying it from the bottom upwards through the heated cylindrical reactor RI (4) which is equipped with a stirrer, located above the outlet for the mixture of organopolysiloxane, catalyst and any additives used exiting from the reactor RI (4) a condenser (8) and a water separator (9) in which, in particular, the water formed in the condensation of Si-bonded hydroxyl groups and volatile organosilicon compounds are condensed and separated, and in a second step conveying the reaction mixture obtained, after leaving the reactor RI (4) at its upper end, continuously from the top downwards through a cylindrical reactor RII (5) which is arranged in a standing position and is operated at the same pressure as reactor RI (4), with there being located at the upper end of the reactor RII (5) an outlet for volatile compounds such as water and volatile organosilicon compounds, which outlet is connected to the condenser (8) optionally connected to a vacuum pump (10) and water separator (9), and in a third step freeing the reaction mixture obtained after exit from the reactor RII (5) at its lower end of catalyst by filtration (7).

Preferably, the product stream from reactor RII is fed to the work-up step by means of a pump (6).

The process of the invention has the advantage that the desired organopolysiloxanes are obtained readily reproducible and in high space-time yields in high purity, with both readily volatile and nonvolatile starting materials being processed in a simple manner.

Furthermore, the process of the invention has the advantage that it shows a high degree of flexibility with regard to the very different types of organopolysiloxanes which can be prepared according to the invention. Thus, organopolysiloxanes of very different viscosity and different contents, or of Si-bonded hydroxyl groups can be prepared in a completely tailored manner by the process of the invention. Also, the process of the invention can be carried out at very different pressures.

The process of the invention has the advantage that water present in the reaction mixture can, by means of the second reaction step, be effectively removed so that undesired reactions of water with organopolysiloxanes can be avoided or substantially reduced.

In the examples described below all parts, percentages and ppm are, unless otherwise indicated, by weight. If not otherwise indicated, the following examples are carried out at the pressure of the surrounding atmosphere, i.e., at about 1000 hPa, and at room temperature, at about 23° C., or at a temperature which is established on combining the reactants at room temperature without additional heating or cooling. The viscosity data are based on a temperature of 25° C.

EXAMPLE 1

A mixture comprising 95.7 parts of α,ω-dihydroxypolydimethylsiloxane having a viscosity of 76 mm$^2$/s and 2.0 parts of acid-activated calcium bentonite (commercially available under the name "Tonsil Optimum FF" from Süd-Chemie AG) and prepared by mixing the starting materials in a make-up vessel (1) with stirring at room temperature is continuously heated to 80° C. via a preheater (3) by means of a gear pump, with 2.3 parts of hexamethyldisiloxane being fed into the line after the make-up vessel, and pumped from the bottom into a cylindrical reactor RI (4) having a length of 430 cm, an internal diameter of 35 cm and a capacity of 277 l. The throughput is 2000 kg/hour. The contents of RI are maintained at 110° C. using a heating jacket (double jacket; 6 bar steam) and mechanically agitated with a paddle stirrer at 210 revolutions/minute. The reaction mixture flows through RI from the bottom upwards and leaves RI at its upper end. The mean residence time in reactor RI is 2.5 minutes. Above the outlet for the reaction mixture there is located a descending condenser (8) (helical heat exchanger, 10 m$^2$) which is connected to a vacuum pump (10) which maintains the interior of RI at a pressure of 50 hPa. The condenser is additionally connected to a water separator (9), where the water formed in the reaction is separated off from the volatile organosilicon compounds condensed in the condenser. The reaction mixture exiting at the upper end of reaction RI flows through reactor RII (5) which has a length of 114 cm, an internal diameter of 51 cm and a utilizable internal volume of 224 l from the top downwards under gravity. Reactor RII is insulated and equipped neither with heating nor with a stirrer. The contents of RII have a temperature of 110° C. At the beginning of the process, RII was empty. At the upper end of the reactor RII there is located an outlet for the volatile constituents of the reaction mixture, which outlet is connected to the above described cooling system comprising condenser (8), water separator (9) and vacuum pump (10) in a manner similar to reactor RI, so that the interior of RII is maintained at a pressure of 50 hPa. After exiting from the lower end of RII (5) the reaction mixture, which is still warm, is separated from the catalyst in a plate pressure filter having a filtration area of 24 m$^2$ and a volume of about 5000 l. The crude product thus obtained is subsequently freed or further volatile constituents, essentially low molecular weight cyclic and linear siloxanes, by means of two short-path distillations at 200° C./1 hPa and 240° C./1 hPa.

Two samples are taken from the product stream a) after exiting from reaction RII at its lower end (sample is immediately filtered through a suction filter) and b) after filtration, analyzed for the Si-bonded hydroxyl group content by means of IR spectroscopy and the viscosity is determined.

In all cases the viscosity is about 93 mm$^2$/s.

| Example | Si-bonded hydroxyl group content [ppm] | |
|---|---|---|
| | Sample 1 | Sample 2 |
| 1 a) | 162 | 132 |
| 1 b) | 147 | 132 |

EXAMPLE 2

The procedure described in Example 1 is repeated, except that the throughput is 1500 kg/h instead of 2000 kg/h, the contents of both reactors RI and RII are at a temperature of 130° C. and the interior of RI and RII is maintained at the pressure of the surrounding atmosphere.

Two samples are taken after completion of the second short-path distillation and analyzed for the Si-bonded hydroxyl group content and the viscosity is determined as described in Example 1.

| Sample | Si-bonded hydroxyl group content [ppm] | Viscosity [mm$^2$/s] |
|---|---|---|
| 1 | 603 | 85 |
| 2 | 663 | 71 |

COMPARATIVE EXAMPLE 1

The procedure described in Example 1 is repeated except that the product mixture exiting from the upper end of the reactor is immediately filtered and distilled. The experiment is carried out both at a throughput of 2000 kg/hour and at 1500 kg/hour.

After the last distillation, a sample is taken and analyzed for Si-bonded hydroxyl group content (silanol content) by means of IR spectroscopy, the viscosity is determined and the volatility of 5 g of sample is determined at 230° C. and the pressure of surrounding atmosphere.

| Throughput [kg/h] | Viscosity [mm$^2$/s] | Volatility [%] | Silanol content [ppm] |
|---|---|---|---|
| 1500 | 124 | 0.16 | <90* |
| 2000 | 113 | 0.13 | 162 |

*90 ppm is the detection limit

COMPARATIVE EXAMPLE 2

A mixture comprising 96.7 parts of α,ω-dihydroxypolydimethylsiloxane having a viscosity of 79 mm$^2$/s and 2.0 parts of acid-activated calcium bentonite (commercially available under the name "Tonsil Optimum FF" from Süd-Chemie AG) and prepared by mixing the starting materials in a make-up vessel with stirring at room temperature is continuously heated to 80° C. via a preheater by means of a gear pump, with 1.3 parts of hexamethyldisiloxane being fed into the line after the make-up vessel, and pumped from the bottom into a cylindrical reactor arranged in a standing position and having a length of 430 cm, an internal diameter of 35 cm and a capacity of 277 l. The throughput is 1600 kg/hour. The contents of the reactor are maintained at 110° C. using a heating jacket (double jacket; 6 bar steam) and mechanically agitated with a paddle stirrer at 210 revolutions/minute. The reaction mixture flows through the reactor from the bottom upwards and leaves it at its upper end. Above the outlet for the reaction mixture there is located a condenser, similar to Example 1, which is connected to a vacuum pump which maintains the interior of the reactor at a pressure of 50 hPa. The condenser is additionally connected to a water separator. The reaction mixture exiting at the upper end of the reactor is separated from the catalyst by filtration. The product is in contact with the catalyst for an additional period of about 3 hours.

One sample is taken from the product stream a) after exiting from the reactor at its upper end (sample is immediately filtered through a suction filter) and b) after filtration, analyzed for the Si-bonded hydroxyl group content by means of IR spectroscopy and the viscosity is determined.

| Example | Viscosity [mm²/s] | Silanol content [ppm] |
|---|---|---|
| C2 a) | 298 | 111 |
| C2 b) | 271 | 216 |

COMPARATIVE EXAMPLE 3

The procedure described in Comparative Example 1 is repeated at a throughput of 2000 kg/h. During the filtration, the product is in contact with the catalyst for an additional period of about 3 hours.

One sample is taken from the product stream
a) after exiting from the reactor at its upper end (sample is immediately filtered through a suction filter) and
b) after filtration, i.e., prior to distillation,
analyzed for the Si-bonded hydroxyl group content by means of IR spectroscopy and the viscosity is determined.

| Example | Viscosity [mm²/s] | Silanol content [ppm] |
|---|---|---|
| C3 a)** | 81 | <90* |
| C3 b) | 67 | 150 |

*90 ppm is the detection limit.
**Sample contained droplets of water; it was therefore dried with Na₂SO₄ and filtered prior to analysis.

COMPARATIVE EXAMPLE 4

90 g of a α,ω-bistrimethylsiloxypolydimethylsiloxane having a viscosity of 1019 mm²/s and an Si-bonded hydroxyl group content, if any, of <90 ppm, below the detection limit, are mixed with 5 g of acid-activated calcium bentonite (commercially available under the name "Tonsil Optimum FF" from Süd-Chemie AG) and 5 g of deionized water.

In a 250 ml three-neck flask fitted with reflux condenser, this mixture is stirred at the temperature given in the table for a period of 2 hours. The catalyst is thereupon filtered off immediately using a suction filter. The viscosity and the Si-bonded hydroxyl group content (IR spectroscopy) of the silicone oil thus obtained are analyzed. The results are shown in the table.

| Temperature [°C.] | Viscosity [mm²/s] | Silanol content [ppm] |
|---|---|---|
| 20 | 996 | <90 |
| 40 | 990 | 114 |
| 60 | 782 | 255 |
| 80 | 619 | 720 |
| 100 | 422 | 1050 |
| 120 | 240 | 1344 |

COMPARATIVE EXAMPLE 5 a) A 1000 ml three-neck flask fitted with stirrer and condenser with water separator is charged with 500 g of a siloxane mixture consisting of 90% of cyclic polydimethylsiloxanes having a cycle size of predominantly from 3 to 20 siloxane units and 10% of a α,ω-dihydroxypolydimethylsiloxane, 15.5 g of hexamethyldisiloxane and 15.0 g of acid-activated calcium bentonite (commercially available under the name "Tonsil Optimum FF" from Süd-Chemie AG).

The mixture is heated to 90° C. at a pressure of 70 hPa. Great delays in boiling prevent continuation of the experiment. Repetition of the experiment in the apparatus described in Comparative Example 1 gives the same result.

b) The experiment described under a) is repeated at the pressure of the surrounding atmosphere and a temperature of 150° C. After 2 hours, the catalyst is filtered off. The siloxane thus obtained is subsequently dried by heating in a flask for a period of 1 hour and 45 minutes at 110° C. and 0.5 mbar. The silicone oil obtained has a viscosity of 99 mm²/s and an Si-bonded hydroxyl group content of 170 ppm.

COMPARATIVE EXAMPLE 6

The procedure described in Comparative Example 1 is carried out using a mixture of 19% of α,ω-dihydroxypolydimethylsiloxane having a viscosity of 75 mm²/s, 19% of hexamethyldisiloxane and 2% of acid-activated calcium bentonite (commercially available under the name "Tonsil Optimum FF" from Süd-Chemie AG), except that the throughput is 1400 kg/hour and
a) the contents of the reactor are at a temperature of 110° C. at a pressure of 130 hPa or
b) the contents of the reactor are at a temperature of 130° C. at the pressure of the surrounding atmosphere.

Delays in boiling occur both in a) and b).

| Example | Yield [kg/h] | Viscosity [mm²/s] | Silanol content [ppm] |
|---|---|---|---|
| C6 a) | 250 | 10 | 120 |
| C6 b) | 650 | 10 | 150 |

What is claimed is:

1. A process for the continuous preparation of organopolysiloxanes by condensation and/or equilibration reaction of organosilicon compounds, which comprises, in a first step
   conveying a mixture consisting essentially of an organosilicon compound and catalyst which is solid in the mixture at least at the reaction temperature continuously from the bottom upwards through a heated cylindrical reactor which is arranged in a standing position and whose contents are optionally mechanically agitated and in a second step
   passing a reaction mixture obtained after leaving the heated cylindrical reactor at its upper end to an initially empty second cylindrical reactor and continuously through the second cylindrical reactor and in a third step
   freeing the reaction mixture of catalyst after exit from the cylindrical reactor.

2. The process as claimed in claim 1, wherein the second cylindrical reactor is arranged in a standing position.

3. The process as claimed in claim 1, wherein the heated cylindrical reactor and the second cylindrical reactor each have a ratio of length to internal diameter of from 1:1 to 50:1.

4. The process as claimed in claim 1, wherein the contents of the second heated cylindrical reactor are at the same or about the same temperature as the contents of the cylindrical reactor.

5. The process as claimed in claim 1, wherein the reaction mixture of the heated cylindrical reactor is stirred.

6. The process as claimed in claim 1, wherein the catalyst is an acid-activated bleaching earth.

7. The process as claimed in claim 1, wherein the heated cylindrical reactor is operated at the same pressure as the second cylindrical reactor.

8. The process as claimed in claim 1, wherein in a first step an organosilicon compound and catalyst are mixed with one another in a make-up vessel with stirring, the mixture thus obtained is then heated via a preheater, using a pump, optional siloxane $R_3SiOSiR_3$ of formula (III) where R is an identical or different optionally substituted hydrocarbon radical is metered into a line after the make-up vessel with the mixture of the organosilicon compound and catalyst and conveyed from the bottom upwards through the heated cylindrical reactor which is equipped with a stirrer, and located above an outlet which provides an exit for the mixture of organopolysiloxane and catalyst is a condenser and a water separator in which, water and volatile organosilicon compounds are condensed and separated, and in a second step a reaction mixture thus obtained in the first step is, after leaving the heated cylindrical reactor at its upper end, conveyed continuously from the top downwards through a second cylindrical reactor which is arranged in a standing position and is operated at the same pressure as the heated cylindrical reactor, with there being located at the upper end of the second reactor an outlet for any remaining water and volatile organosilicon compounds, which outlet is connected to the condenser and water separator of step one, and in a third step the reaction mixture obtained is, after exiting from the second reactor at its lower end, freed of catalyst by filtration.

* * * * *